United States Patent [19]
Ozenne et al.

[11] Patent Number: 5,364,379
[45] Date of Patent: Nov. 15, 1994

[54] STOMA EQUIPMENT

[75] Inventors: Jean-Pierre Ozenne, Coye la Forêt; Henri Holtermann, St. Jean De Luz, both of France

[73] Assignee: Laboratoires Biotrol, Paris Cedex, France

[21] Appl. No.: 711,327

[22] Filed: Jun. 6, 1991

[30] Foreign Application Priority Data

Jun. 8, 1990 [FR] France .................. 90 07140

[51] Int. Cl.⁵ .............................. A61F 5/448
[52] U.S. Cl. ........................ 604/342; 604/344
[58] Field of Search .............. 604/332–345; 383/66, 96; 215/279

[56] References Cited

U.S. PATENT DOCUMENTS

| | | | |
|---|---|---|---|
| 985,856 | 3/1911 | Taylor | 215/279 |
| 3,190,679 | 6/1965 | Lester | 285/8 |
| 4,319,571 | 3/1982 | Winchell | 604/342 |
| 4,889,534 | 12/1989 | Mohiuddin et al. | 604/339 |
| 4,917,691 | 4/1990 | Briggs | 604/339 |
| 5,026,360 | 6/1991 | Johnsen et al. | 604/339 X |

FOREIGN PATENT DOCUMENTS

| | | |
|---|---|---|
| 0163979 | 12/1985 | European Pat. Off. . |
| 0171255 | 2/1986 | European Pat. Off. . |
| 0347025 | 12/1989 | European Pat. Off. . |
| 2626464 | 8/1989 | France . |
| WO8703192 | 6/1987 | PCT Int'l Appl. . |
| 9101118 | 2/1991 | PCT Int'l Appl. ......... 604/342 |

Primary Examiner—Randall L. Green
Assistant Examiner—Mary Beth O. Jones
Attorney, Agent, or Firm—Lackenbach, Siegel, Marzullo, Aronson & Greenspan

[57] ABSTRACT

Stoma equipment comprising a bag-carrier for fixing around an artificial opening in the body of a user by means of a base plate provided with an adhesive or with a pressure-sensitive adhesive rubber or with any equivalent means, together with a bag for collecting body wastes and/or fluids and suitable for being removably assembled to a sleeve or collar of the bag carrier by means of a rim on the bag, wherein the bag is fixed on the bag-carrier by deforming sealing means whose radial size is increased by operating an appropriate actuator device.

32 Claims, 14 Drawing Sheets

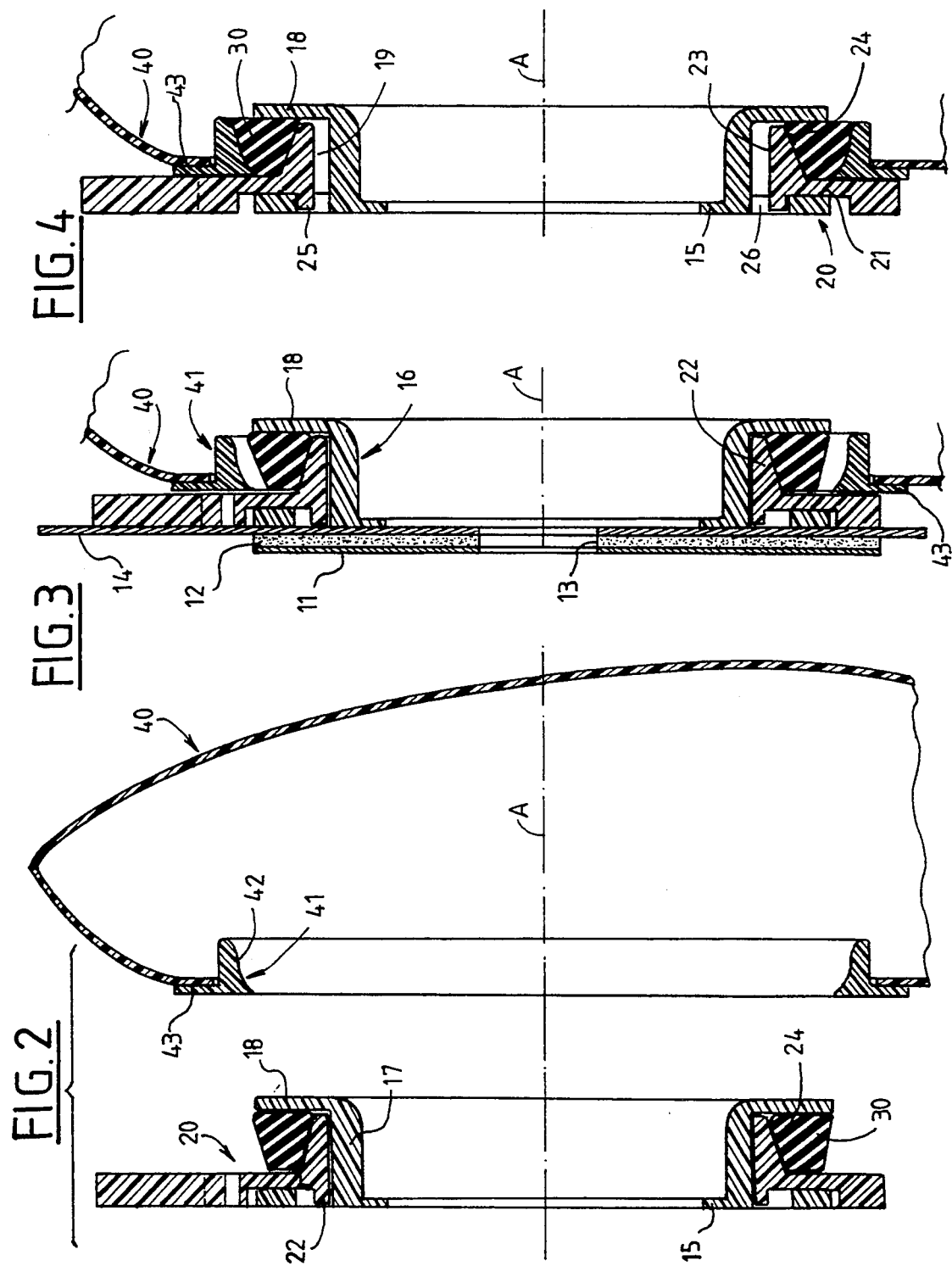

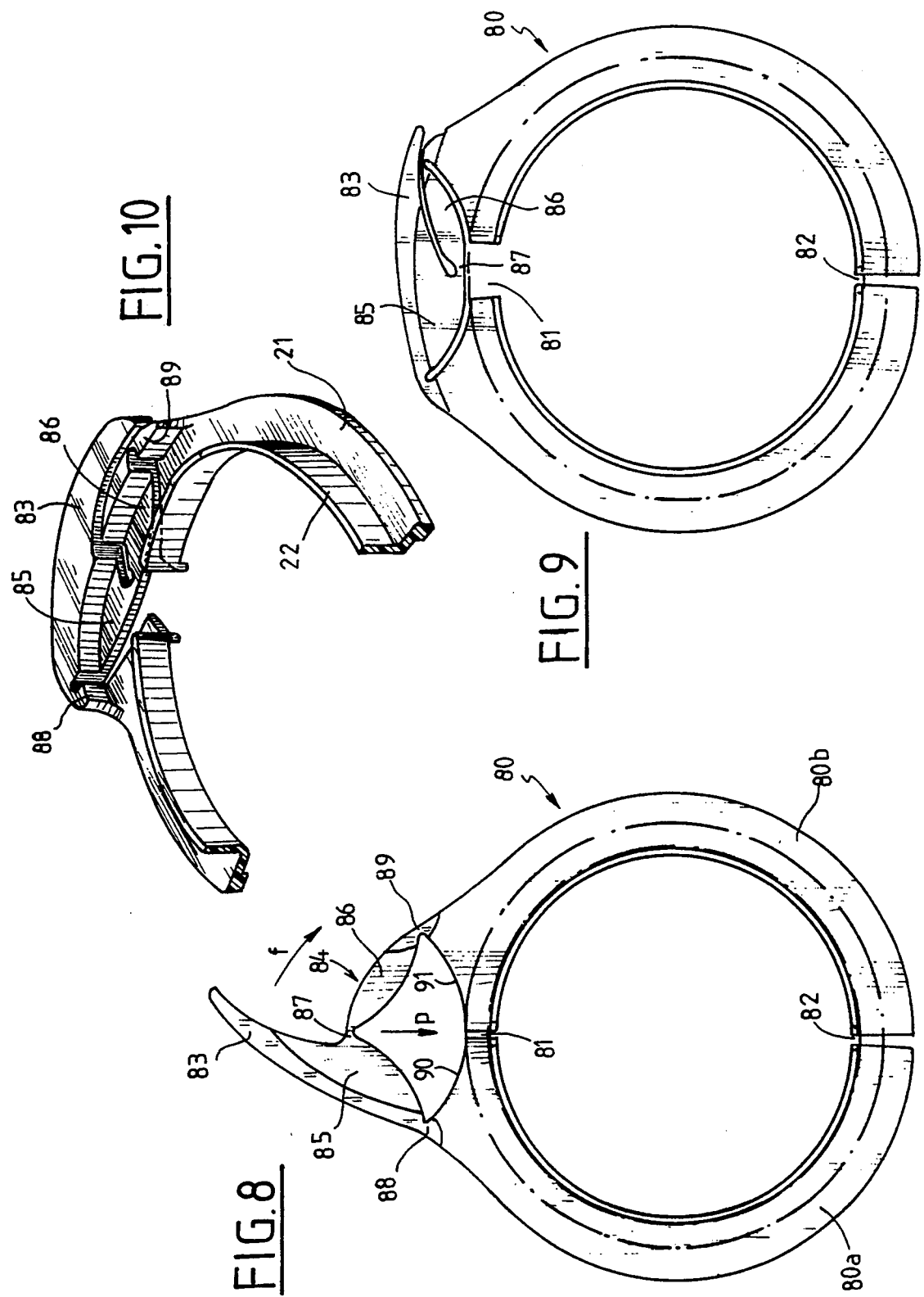

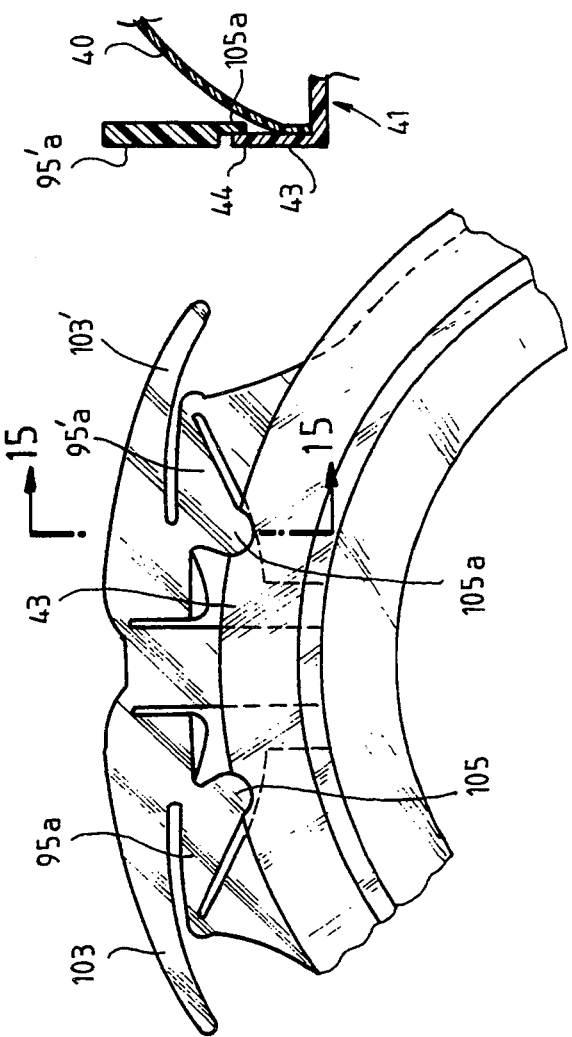
FIG.15
FIG.14
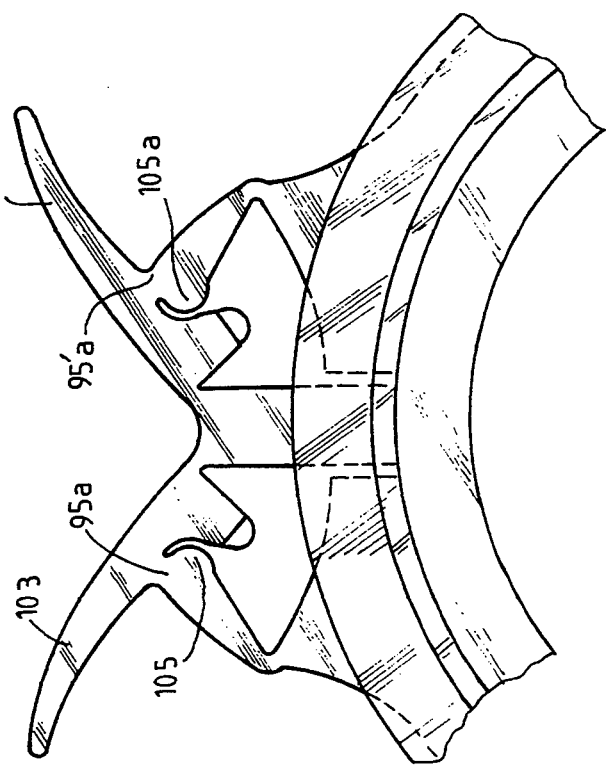
FIG.13

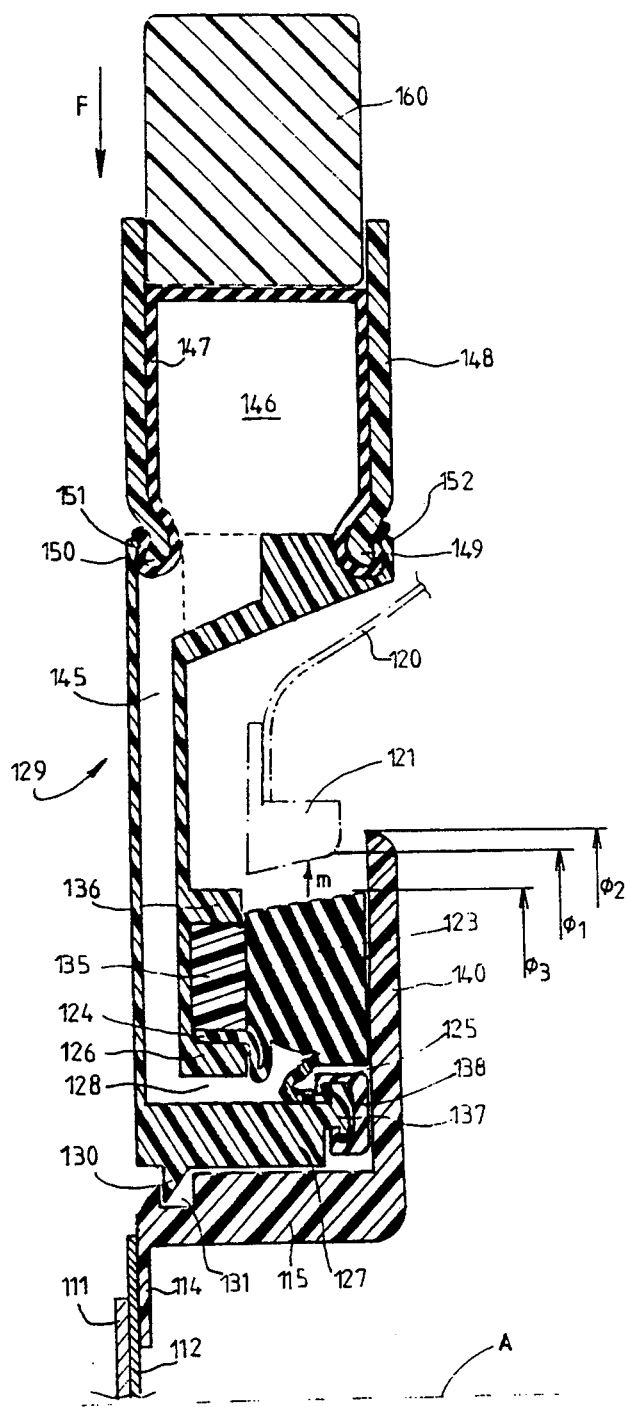
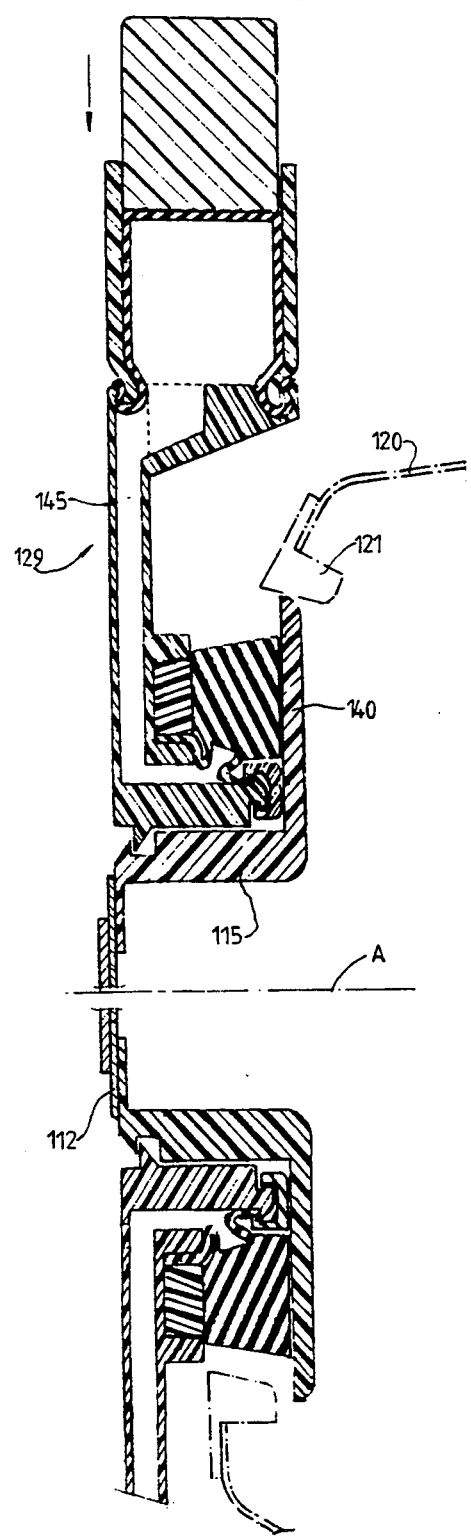

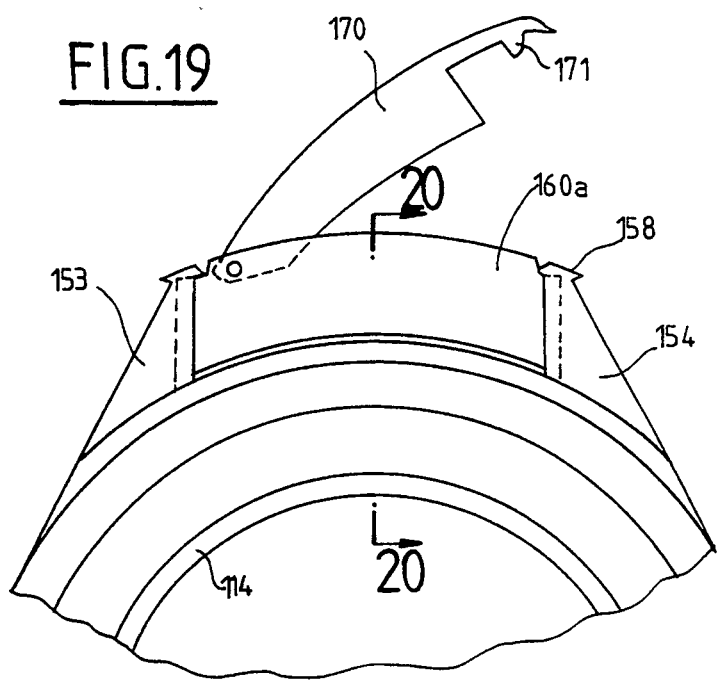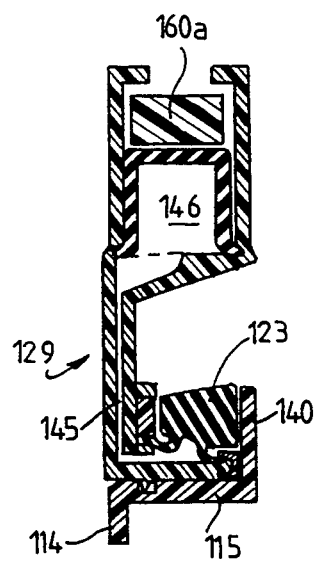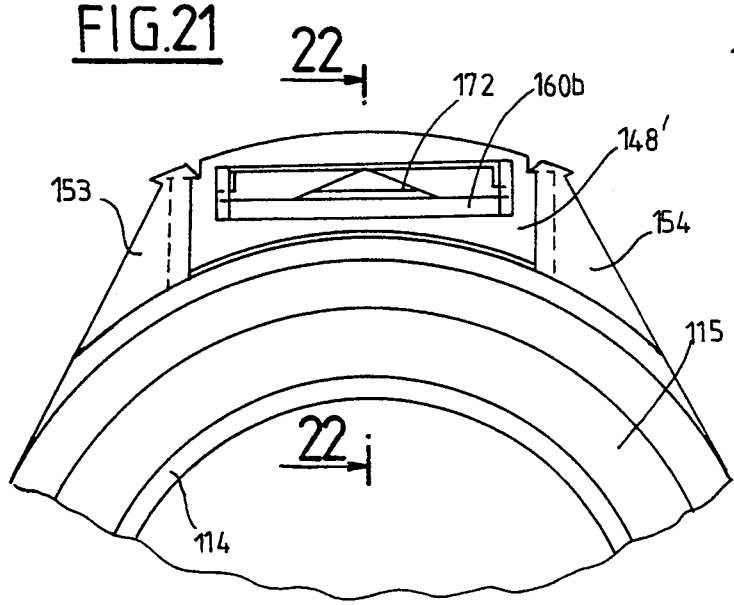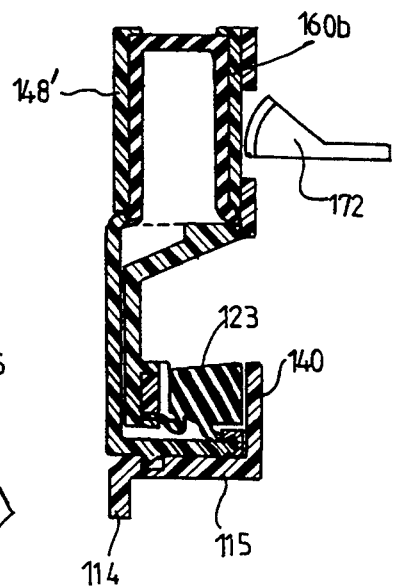

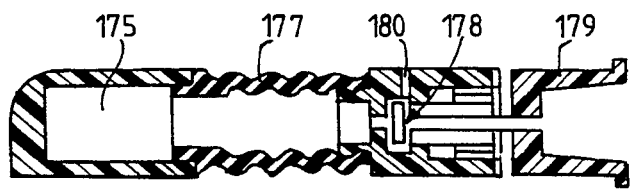
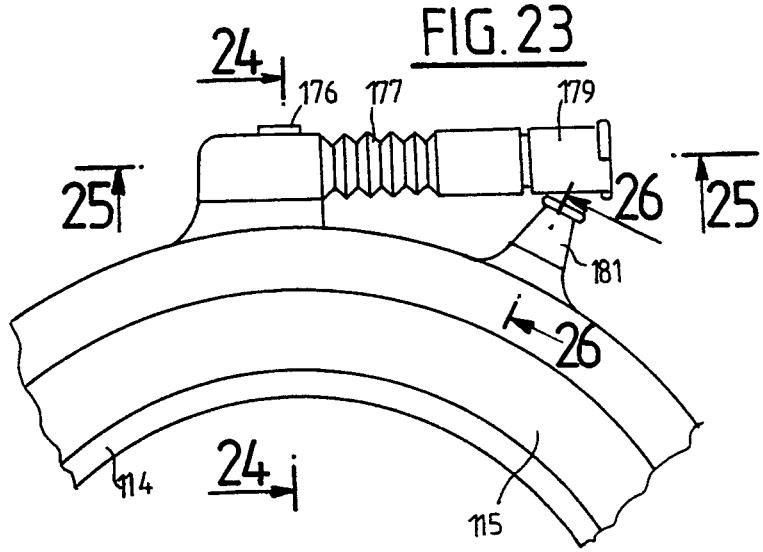
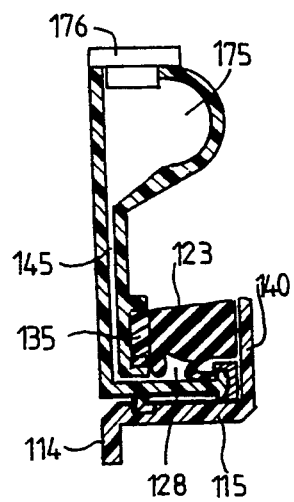
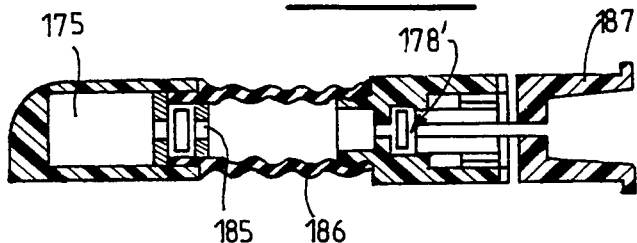

STOMA EQUIPMENT

The present invention relates to stoma equipment and more particularly it relates to a system for assembling a stoma bag to a bag-carrier.

BACKGROUND OF THE INVENTION

Numerous types of equipment have already been proposed for collecting body wastes or urine from people who have been subjected to surgical operations such as enterostomy (ileostomy, colostomy, . . . ) or urostomy. This prior equipment includes systems constituted by single-use bags which are generally fixed directly to the skin of the user by an adhesive in the form of a ring or which are provided with a skin protector, and "two-part" systems in which the collection bag (which may be disposable or reusable) is removably coupled to a protective front plate itself fixed to the body of the user by means of a belt or a base plate provided with an adhesive or with adhesive rubber. Systems of the second-mentioned type must satisfy certain necessary conditions, some of which are mutually contradictory. The collector bag should be fixed onto the bag-carrier or protective front plate in such a manner that no significant pressure is applied to the region around the stoma which is sensitive and generally painful, while nevertheless ensuring a reliably leakproof connection when the system is assembled, but still allowing the parts of the system to be disaaembled easily, although never accidentally. In addition, the equipment should not give rise to peristomal skin complications, it should be as unobtrusive as possible, and it should be capable to being fitted to patients of very different morphologies. It is also desirable that, after receiving instruction from medical personnel, patients should themselves be capable of installing collection bags on their bag-carriers, and this naturally requires the operations of assembling and disassembling the bag and the bag-carrier to be as simple and as easy as possible, particularly for elderly users.

Thus, in an attempt to provide a solution to the problem posed, proposals have recently been made (in FR-A1-2 626 464, for example) to provide a two-part system in which the means for coupling the bag to the bag-carrier are constituted by a deformable collar and a split ring designed to clamp around the collar, and a short tube whose outside dimension is substantially equal to the inside dimension of the collar which is suitable for being slidably inserted into the collar or withdrawn therefrom when the ring is in an open position, such that when the ring is in a clamped position around the collar, the collar is deformed against the tube. It is relatively difficult to manufacture this system given that the diameters of the tube and of the collar must be made to very accurate tolerances so that a leakproof assembly is obtained by relatively little deformation of the collar, whose channel section normally hinders such deformation, Similar difficulties exist in very numerous proposed systems of the interfitting type, e.g. as described in EP-A-0 171 255, or the type described above, and it will be understood that in spite of the variety of solutions that are already known, the problem remains of providing improved stoma equipment capable of satisfying the various requirements for such equipment and also making it possible to place the bag in a desired direction relative to the bag-carrier, as may be desirable for increasing user comfort. Although this bag direction problem has already been considered, e.g. in EP-163 979, the solutions proposed are not entirely satisfactory, neither with respect to the way the parts are assembled nor with respect to leakproofing and/or the size of the devices for connecting the bag to its support.

Consequently a general object of the invention is to provide such equipment which is applicable to digestive or urinary stomata while satisfying the above conditions, and in which it is firstly extremely easy to install a bag on a bag-carrier previously fixed to the body of a user, and secondly in which this can be done while applying practically no pressure to the region adjacent to the stoma.

Another object of the invention is to provide such equipment which is very safe in use and, in particular, in which the leakproofing of the connection between the bag and the bag-carrier is reinforced whenever the pressure inside the bag increases.

SUMMARY OF THE INVENTION

The problem is solved in a two-part type stoma equipment comprising a bag-carrier for fixing to the body of a user by means of a base plate provided with an adhesive or with a pressure-sensitive adhesive rubber or with any equivalent means, together with a bag for collecting body wastes and/or fluids and suitable for being removably assembled to the bag-carrier by means of a rim on the bag, wherein, according to the invention, the bag is fixed on the bag-carrier by deforming sealing means whose radial size is increased by operating an appropriate actuator device.

Consequently, in such equipment and in contrast to the prior system described in FR-A1 2 626 464 or to systems of the interfitting type, no pressure is exerted in the vicinity of the stoma while the bag is being installed on the bag-carrier, given that the rim of the bag is larger in size than the corresponding part of the bag-carrier with which is co-operates and which surrounds the stoma when in use.

In addition, in the equipment of the invention, the rim of the bag is inside the bag proper, thereby avoiding a "sticking" effect between the bag-carrier and the sheet constituting the bag, which "sticking" sometimes prevents body waste being evacuated satisfactorily.

In the first embodiment of apparatus of the invention, the actuator device is a split ring which is associated with the sealing means constituted by a sealing ring of resilient material interposed between the bag rim and the split ring when the bag is applied to the bag-carrier.

In one form of this first embodiment, the split ring is integrally formed with actuator means constituted by a lever hinged on the split ring and controlling a toggle type mechanism.

The split ring and the actuator means are preferably molded in a plastics material having mechanical and resilient properties enabling them to constitute the fulcrums of the lever and of the toggle mechanism by a hinge effect.

In this particular form, the single part constituting the split ring and its actuator means is molded in its configuration corresponding to the large size of the split ring.

In another embodiment, the actuator device is constituted by two half-rings are associated with the sealing means made of resilient material interposed between the bag rim and the half-rings when the bag is placed on the bag-carrier.

Preferably, each half-ring is integral with actuator means constituted by a lever hinged thereto and controlling a toggle mechanism.

In another embodiment, the two half-rings are connected to each other by a toggle mechanism, itself constituted by two arms which are hinged to each other about a hinge and which are hinged to respective ones of the half-rings by hinges, the first of which also constitutes the fulcrum of a lever.

In a variant, the two half-rings are interconnected by two toggle mechanisms, each constituted by a pair of arms, hinged together about a hinge and hinged to the half-rings via respective hinges, fulcrums for levers being formed about two hinge axes fixed to the flange by a part.

The sealing ring may have a trapezium-shaped right cross-section and is engaged around a lip on the split ring, deformation of the split ring during operation of the actuator means deforming the sealing ring until it is applied in leakproof manner against the bag rim.

Advantageously, the bag rim is made of a plastic material that is rigid enough to accept the clamping force developed by the sealing ring with which its inside face of generally hyperbolic section co-operates when the bag is assembled to the bag-carrier.

To mount the actuator device on the bag-carrier, the bag carrier has groove delimited by a collar which surrounds the stoma when the equipment is in use, and by two flanges which are substantially parallel to each other and perpendicular to the axis of the collar, a first one of the flanges co-operating in retaining the sealing ring and a second one of the flanges serving firstly to fix the bag-carrier to the base plate and secondly to guide and/or retain the actuator device on said bag carrier.

This latter function is most simply provided by the second flange being provided with slots which receive studs on the split ring.

In another embodiment, the sealing means is a split ring shaped to have projections at its periphery suitable for co-operating with hollows or a groove of complementary shape provided in the bag rim.

In such an embodiment the split ring is mounted on the bag carrier in a groove formed in an endpiece thereof, the endpiece including a flange with a tapering outside face suitable for co-operating with a complementary face on the rim of the bag, and the actuator means is advantageously constituted by a lever which displaces one of the ends of the split ring which includes tabs or the like for engaging recesses of the lever for the purpose of lcoking the lever in the position where the bag is assembled to the bag-carrier.

In yet another embodiment, a single elastically deformable member acts both as the actuator device and as the sealing gassket, either on its own or by means of a sealing ring which is directly associated therewith.

In one form of this embodiment, the member used is a ring suitable for deformation by means of a fluid (pneumatic or hydraulic) to increase its radial size when sealing the rim of the bag to the bag-carrier.

In another form, the member is a toroidal chamber that is inflatable and deflatable via a valve associated therewith, said chamber itself constituting he sealing gasket, or in a variant including an auxiliary sealing gasket.

As inflation means, the invention provides for a syringe type device or else a supply of gaseous fluid under pressure such as a portable compressed air cylinder, or a hydraulic device in which the displacement of a lever serves to transfer a given volume of liquid to and from the chamber to be inflated.

Although it is a "two-part" type of system, the stoma apparatus of the invention is thus constituted by at least three items, namely: a bag carrier including a sleeve or a collar; a bag having a relatively rigid rim; and an elastically deformable member acting to prevent the rim of the bag moving relative to the collar whenever the dimensions of said deformable member are increased by mechanical, hydraulic, or pneumatic actuator means.

In another embodiment of equpoment of the the invention, the radial size of the sealing means comprising a sealing ring per se mounted to move radially relative to the sleeve of the bag-carrier is increased by being moved outwardly relative to said sleeve when the volume of a chamber adjacent to the ring is increased.

In a first form of this embodiment, the volume of the chamber adjacent to the sealing ring is increased by inserting a quantity of fluid into said chamber in addition to the fluid that it contained initially.

Said insertion may be obtained by mechanical means such as locally deforming a space of given volume by means of a lever or the like, or in a variant by directly or indirectly conveying a hydraulic or a pneumatic fluid into said chamber from a source of fluid under pressure such as a syringe, a pump, a supply of compressed gas, etc.

The space may be delimited by a wall of resilient material against which a piston is disposed to act, displacement of the piston being controlled by actuating one or more levers.

The space may be enclosed in a box fixed to the bag-carrier by brackets, and said brackets may have hooks suitable for co-operating with complementary hooks on the piston actuating lever(s) to hold said lever(s) in a position corresponding to the bag being assembled to the bag-carrier.

In another embodiment, the space for feeding the variable volume chamber adjacent to the sealing ring via the channels may be connected to a source of fluid under pressure by a valve device via a flexible deformable tube.

In another form, the valve device is connected to a non-return valve, itself connected to a beloows type tube for inflating the space by means analogous to a pump.

In another embodiment of the invention, the sealing means is a hollow or solid component including lips or membranes for fixing to a body integral with the bag-carrier, and including means for changing the volume of the chamber adjacent to said sealing ring.

In one form of this embodiment, the body has channels opening out into an enclosure whose volume can be changed and/or into which a fluid under pressure may be injected.

In yet another embodiment, the radial size of the sealing means is increased by a split ring acting by a wedging effect via a washer adjacent to said sealing means, which sealing means is then advantageously constituted by a toroidal member having a somewhat trapezium-shaped right cross-section and enclosing an angular cavity filled with a liquid or gaseous fluid.

In a variant, the sealing means is a solid member of cellular material having an integral surface skin obtained using techniques known in the manufacture of foam or cellular type materials in the elastomer and/or plastomer industry.

In another variant, the sealing means is a solid or hollow ring having a polygonal right cross-section and made of a relatively soft elastomer type material, advantageously having hardness lying in the range 20 to 40 in the Shore A scale.

When the equipment includes a split ring for increasing the radial size of the sealing means, the ends of the ring advantageously include actuator lugs enabling said ends to be moved towards each other, together with means such as latches hooks, catches, or the like for holding said split ring in its open position or in its closed position.

In addition, the invention also provides for associating a tongue with one of the lugs of said split ring, said tongue being slidably received in a passage through the other lug to guide said lugs relative to each other during motion towards each other and away from each other.

Whatever the embodiment, the invention provides for the sealing means to be associated with a support that may be mounted to rotate relative to the sleeve of the bag-carrier, such that one the bag has been applied thereto, it can be pointed in any direction relative to the bag-carrier as is sometimes desirable to increase user comfort.

In a variant, the support for the sealing means is not mounted to rotate relative to the bag-carrier sleeve, and the direction in which the bag points relative to the bag-carrier can be varied after the bag has been mounted on the bag-carrier by slightly reducing the radial dimension of the sealing means, thereby reducing the pressure with which the bag is applied against the bag-carrier.

In an advantageous embodiment, the bag-carrier has a flange which holds the sealing means against axial displacement, with the inside diameter of the rim on the bag being smaller than the outside diameter of the flange but larger than the outside diameter of the sealing means.

The invention also provides a bag for collecting body wastes and/or fluids, in particular for enterostomy or urostomy, and suitable for forming a part of equipment as defined above.

The invention also provides a bag-carrier suitable for forming a part of such a system.

BRIEF DESCRIPTION OF THE DRAWINGS

Embodiments of the invention are described by way of example with reference to the accompanying drawings, in which:

FIG. 2 is a fragmentary longitudinal section through a bag-carrier and a bag constituting a first embodiment of equipment of the invention;

FIG. 3 is a view analogous to FIG. 2 showing the bag applied to the bag-carrier but prior to being fixed thereto;

FIG. 4 is a view analogous to FIG. 3 but after the bag has been fixed to the bag-carrier;

FIG. 8 is an elevation view of a component part of yet another embodiment of the invention, said part being shown in a first condition;

FIG. 9 is a view analogous to FIG. 8, showing the part in another condition;

FIG. 10 is a fragmentary perspective view of said part;

FIG. 13 is a fragmentary view analogous to FIG. 11 but on a larger scale and showing a variant;

FIG. 14 is a fragmentary view analogous to FIG. 12, but for the variant shown in FIG. 13;

FIG. 15 is a diagrammatic section on line 15—15 of FIG. 14;

FIG. 17A is a view analogous to FIG. 17, but showing a variant embodiment;

FIG. 17B shows how a bag is installed on a bag-carrier;

FIG. 19 is a fragmentary view analogous to FIG. 16 but showing another embodiment;

FIG. 20 is a section view on line 20—20 of FIG. 19;

FIG. 21 is a view analogous to FIGS. 16 and 19, but for yet another embodiment;

FIG. 22 is a section view on line 22—22 of FIG. 21;

FIG. 23 is a view analogous to FIGS. 19 and 21, but for another embodiment;

FIG. 24 is a section view on line 24—24 of FIG. 23;

FIG. 25 is a section view on line 25—25 of FIG. 23, but on a larger scale;

FIG. 26 is a section on line 26—26 of FIG. 23;

FIG. 27 is a diagrammatic view analogous to that of FIG. 25, but showing a variant embodiment;

DETAILED DESCRIPTION

Figure 1:
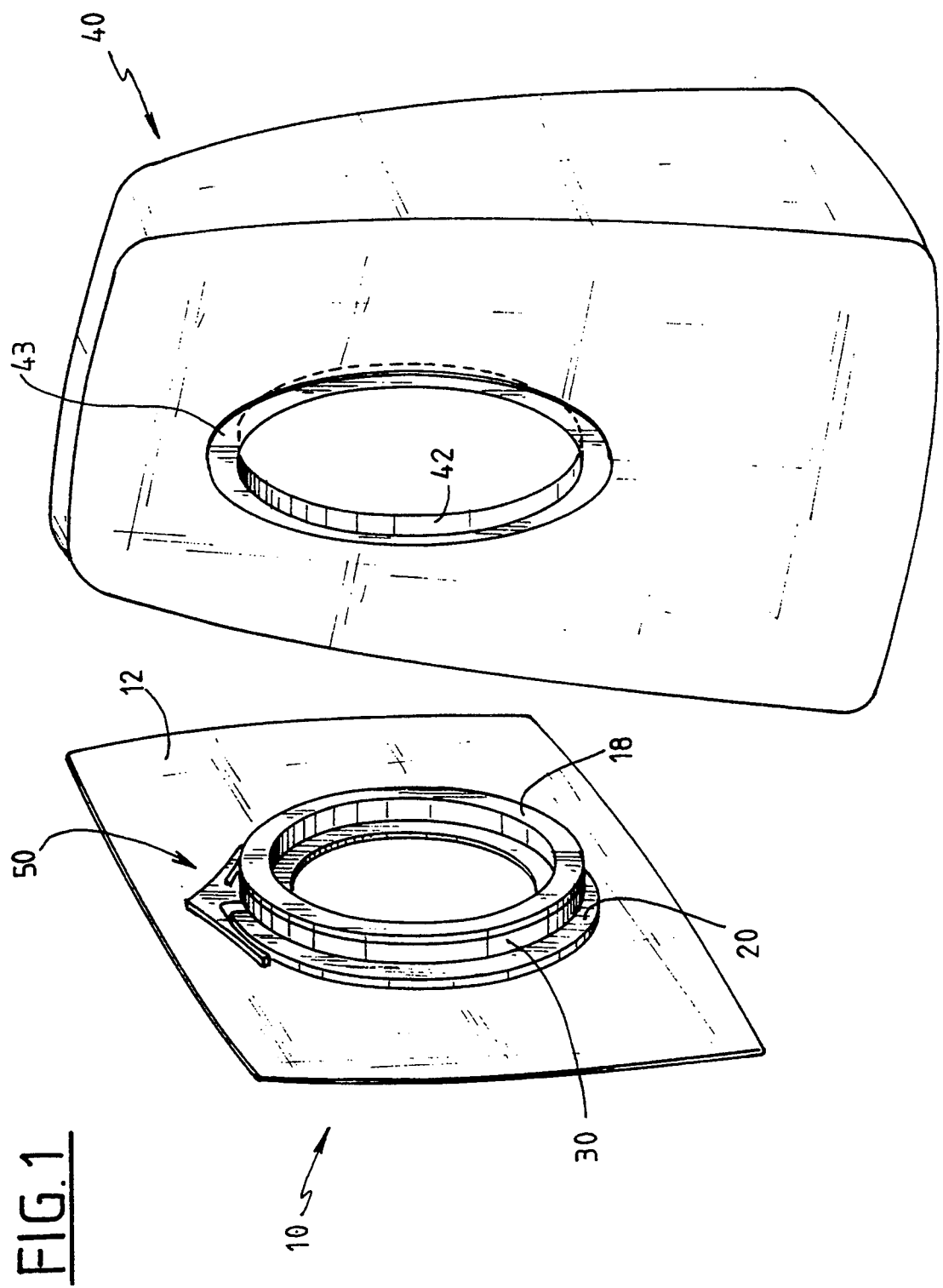
FIG. 1 is a diagrammatic perspective view of a bag-carrier and a bag constituting equipment of the invention and shown at a distance from each other.

Reference is made initially to FIGS. 1 to 4 which show a first embodiment of two-part type stoma equipment of the invention, i.e. equipment including bag-carrier 10 for fixing around an artificial opening in the body of a user by appropriate fixing means. Such means may comprise a base plate 12 provided with adhesive or with a pressure-sensitive adhesive rubber (known per se) that is protected for as long as the equipment is not in use by means of a peel-off film 11 (FIG. 3). In a variant and/or in addition, the bag-carrier 10 may be held on the body of the user by means of a belt (not shown) or by analogous means. The bag-carrier 10 whose base plate 12 includes an opening 13 that surrounds the stoma when the equipment is in use also includes an adhesive composite sheet 14 on the face of the base plate 12 opposite to its face that comes into contact with the body of the user. The composite sheet 14 contributes to protecting the peristoma region and to holding the plate against the skin of the user. An endpiece 16 comprising a sleeve or collar 17 which is cylindrical about an axis A has a first flange 15 which is fixed to the face of the composite sheet 14 that is opposite to its face connected to the base plate 12, and a second flange 18 which is substantially parallel to the flange 15 (both of which are perpendicular to the axis A), with the two flanges 15 and 18 together defining a groove 19.

The groove is designed to receive a deformable ring 20, e.g. a split ring comprising a substantially plane body 21 of circular outline delimited on the inside by a lip 22 at right angles having a cylindrical inside surface 23 and a tapering outside surface 24 (FIGS. 2 and 4). According to the invention, the ring 20 is the device which serves to hold the bag 20 on the bag-carrier 10 by increasing its size (with size being increased in a manner explained below). The ring is held and guided relative to the flange 15 by studs 25 on the ring that are received in slots 26 in the flange 15.

The lip 22 of the deformable ring 20 carries a sealing gasket or ring 30 made of resilient material (advantageously a thermoplastic elastomer (TEP) having a right cross-section that is generally trapezium-shaped and whose thickness parallel to the axis A is substantially equal to the distance between the flanges 15 and 18 minus the thickness of the split ring, such that the sealing ring 30 is also received in the groove 19. The largest nominal outside diameter of the sealing ring 30 is less than the smallest diameter of the rim 41 of the bag 40 so that the bag can be installed with the bag rim surrounding the sealing gasket or ring 30 without applying pressure to the zone surrounding the stoma. It is then possible to fix the bag 40 to the bag-carrier 10 by deforming the split ring 20 to increase its dimensions, thereby also increasing the dimensions of the sealing ring 30 so that it bears against, and has a clamping effect on, the inside surface 42 of the bag rim 41 which has a generally hyperbolic right cross-section facing the inside of the bag 40 and which is made of a relatively rigid material, e.g. polypropylene or high density polyethylene.

To do this and bring the equipment into the condition shown in FIG. 4, the invention provides for associating the deformable ring 20 with appropriate actuator means. In the embodiment shown and described, the actuator means 50 is constituted as a lever suitable for moving the adjacent ends of the split ring apart and for locking the equipment in this operating position, which can be done most simply by making tabs or the like at the periphery of the split ring co-operate with recesses on the inside edge of the lever.

Performing the opposite operation on the lever 50, i.e. returning the split ring 20 to its initial, small-sized condition makes it possible to withdraw the bag 40 from the bag carrier 10.

The bag 40 for collecting body wastes and/or fluids suitable for evacuation through the endpiece 16 may be of the disposable type, or it may be emptiable. In either case it is made by fixing an outwardly-directed flange 43 on the bag rim 41 to the bag per se by gluing, welding, or the like. The bag is constituted by a sheet of polyethylene, or of PVC, or of polyamide, or else by a composite barrier sheet of the polyethylene/EVA/PVC/EVA/polyethylene type such as those known under Dow Chemical's trademark Saranex, or a composite sheet of the EVA/EVA-vinylidene polychloride copolymer type such as those known under Grace's trademark Cryovac, or indeed a composite sheet of the EVA/EVOH/EVA type, or of an analogous material.

Operation of the equipment is simple and reliable, and highly satisfactory operation has been obtained for an embodiment comprising an endpiece 16 having a diameter of about 55 mm, a bag rim having an inside diameter of about 68 mm, and a sealing gasket or rim having an outside diameter of about 66 mm.

Figure 6:
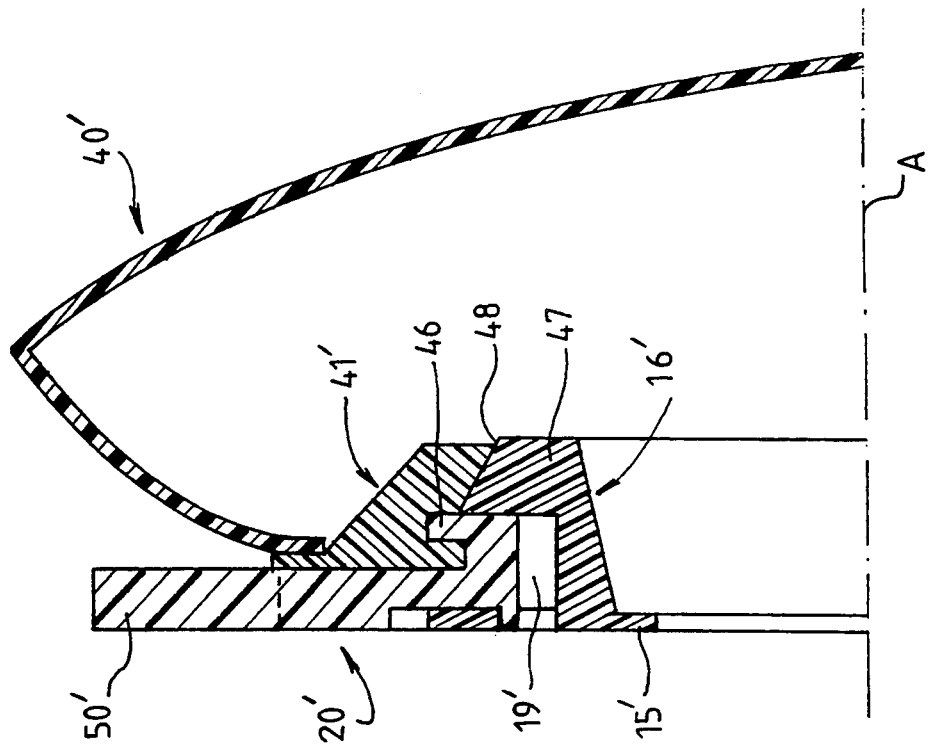
FIG. 6 is a view analogous to FIG. 4 but corresponds to the embodiments shown in FIG. 5.
Figure 5:
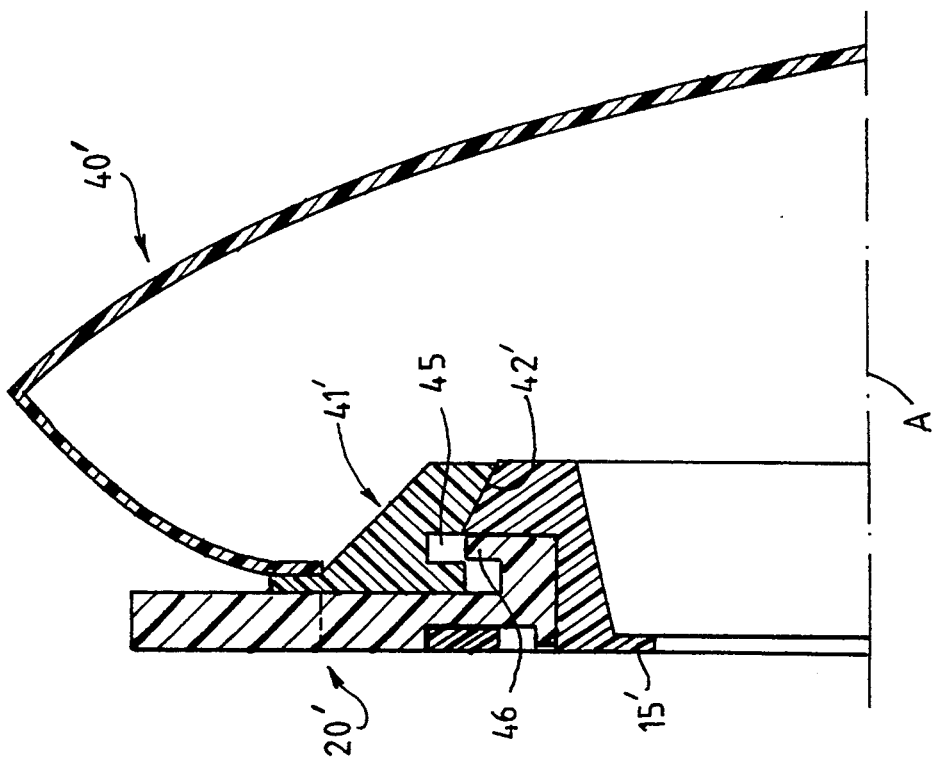
FIG. 5 is a fragmentary view analogous to FIG. 3 but applicable to a different embodiment.

Reference is now made to FIGS. 5 and 6 which are diagrams of another embodiment. In this embodiment, the bag 40' is welded or glued to the bag rim 41' that projects towards the inside of the bag and that is shaped to have an inwardly tapering inside surface 42' whose larger-diameter end is indented to form hollows or a groove 45. Radial projections 46 of a deformable member 20' mounted on the bag-carrier in a groove 19' of its endpiece 16' are suitable for co-operating with the hollows or groove 45. The endpiece has a flange 15' analogous to the flange 15 of the above-described embodiment and is designed to co-operate with the bag rim 41' by means of a rib 47 whose tapering outside surface 48 is complementary to the inside surface 42' of the bag rim. In this embodiment, the member 20' which is enlargeable by being deformed is likewise a split ring made of plastic and is advantageously integrally molded with actuator means 50 enabling its dimensions to be increased so as to go from the condition shown in FIG. 5 to the condition shown in FIG. 6 which is the condition in which the bag 40' is fixed to the bag-carrier.

In order to install such equipment, the bag-carrier is initially fixed to the body of the user by means of a base plate 12 provided with an adhesive or with an adhesive rubber and by the sheet 14 (naturally after the protective film 11 has been removed). The bag 40' is installed by being presented to the bag-carrier with the bag rim 41' being engaged on the rib 47 while applying practically no pressure to the zone adjacent to the stoma. Actuating the lever 50' to increase the dimensions of the ring 20' causes the projections 46 thereon to penetrate into the hollows or groove 45, thereby holding the bag 40' in leakproof manner on the bag-carrier by co-operation between the complementary tapering surfaces 42' and 48.

The bag 40' is separated from the bag-carrier by the opposite procedure of unlocking the lever 50' and then moving it in the opposite direction to that described above.

Figure 7:
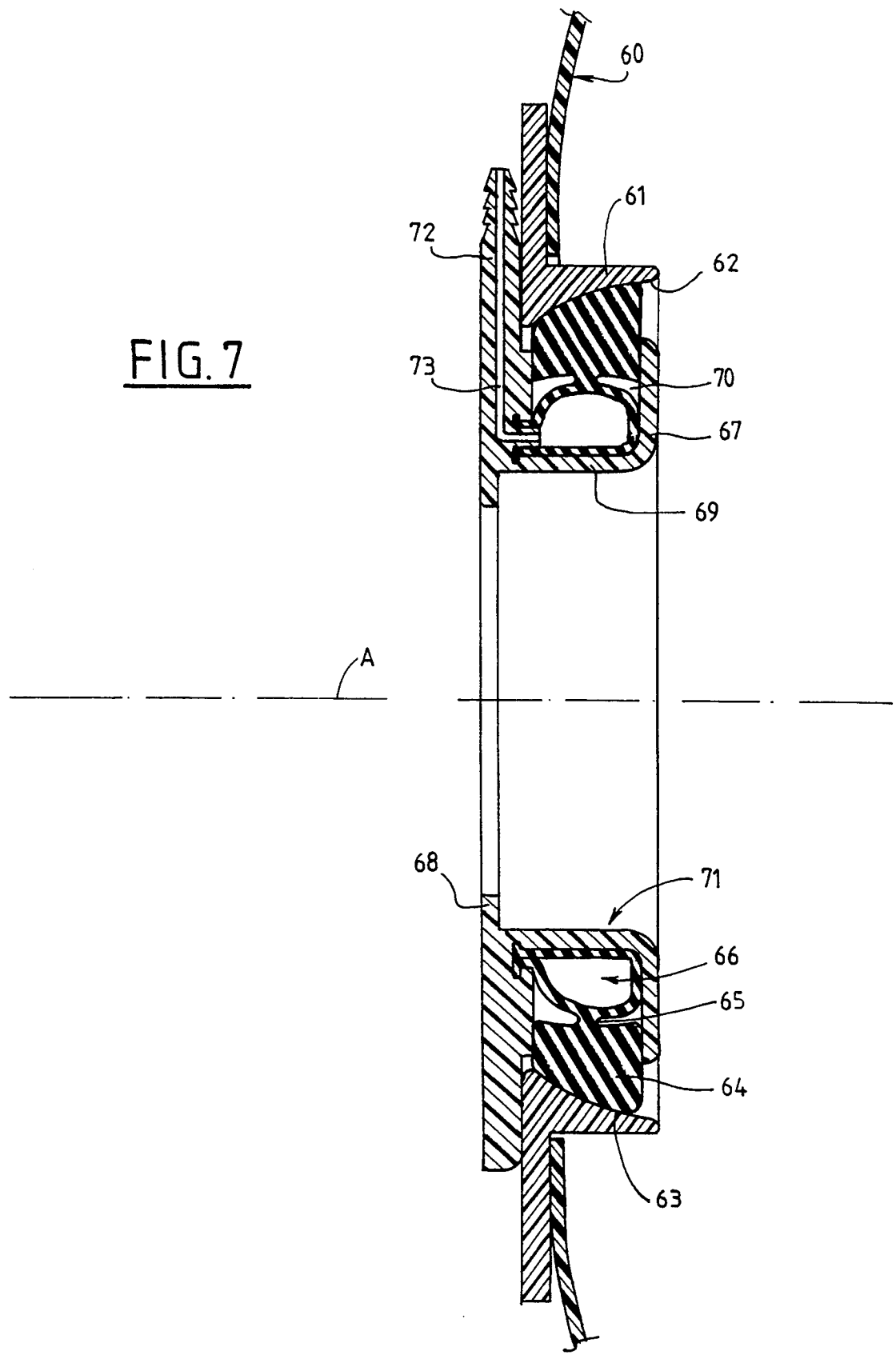
FIG. 7 is a view analogous to FIGS. 4 and 6 but applies to yet another embodiment.

The invention is not limited in any way to the embodiments and the application described above. Thus, as shown in FIG. 7, the invention provides for embodiments in which the bag is fixed to the bag-carrier by deforming a member whose size is increased by means of a hydraulic or a pneumatic fluid. In the embodiment shown, the bag 60 has an inwardly-directed bag rim 61 whose inside surface 62 is curved, e.g. following a hyperbolic outline. The outside surface 63 of a sealing ring 64 of trapezium-shaped right cross-section is suitable for co-operating with the inside surface of the rim. The sealing ring is made of resilient material, e.g. a thermoplastic elastomer (TEP) and it is connected by an isthmus 65 to a toroidal chamber 66 received in the groove 70 formed on an endpiece 71 of the bag-carrier, which groove extends between a cylindrical collar about an axis A, an outside flange 67, and an inside flange 68, which flanges are substantially parallel to each other and perpendicular to the axis A. The resiliently deformable chamber 66 is advantageously made of the same material as the sealing ring 64 and is connected to an endpiece 72 having a through channel 73 including a valve (not shown).

The operation of this embodiment is immediately obvious from the above. Once the bag-carrier has been fixed to the body of the user and the chamber 66 has been deflated, the bag 60 is presented to the bag-carrier with the bag rim 61 being easily installed on the sealing ring 64. The endpiece 72 which is fixed to the bag-carrier is then engaged with pneumatic or hydraulic inflation means 66' such as a syringe device, a supply of gaseous fluid under pressure such as a portable compressed air cylinder, or a device in which displacing a lever serves to transfer a given volume of liquid into the chamber 66 via the channel 63. As a result, the volume of the chamber 66 increases and the ring 64 is pressed against the bag rim 61 so as to fix the bag 60 in leakproof manner to the bag carrier.

The opposite procedure is applied to separate the bag from the bag-carrier once the pressure of the pneumatic or hydraulic fluid in the chamber 66 has been removed.

Reference is now made to FIGS. 8 to 10 which show a preferred embodiment of equipment of the invention in which the device for fixing the bag to the bag-carrier is a split ring made of plastic and integrally molded with the ring actuator means. In this embodiment, the structure of the bag and the structure of the bag-carrier are substantially the same as the embodiment described with reference to FIGS. 1 to 4 and the same references designate parts that are similar. As can clearly be seen in FIGS. 8 and 9, the ring 80 is split into two diametrically opposite regions 81 and 82, with the two resulting half-rings 80a and 80b being interconnected by a lever 83 and a toggle type mechanism 84 whose two branches 85 and 86 are hinged together about a hinge 87 and are also hinged about respective hinges 88 and 89 to the half-ring 80a and to the half-ring 80b, with the hinge 88 also constituting the fulcrum of the lever 83. The lever is integrally molded with the split ring 80 while the ring is in its largest dimension configuration as shown in FIG. 9, i.e. the configuration in which the lever is moved down to come into contact with the arm 86 which then lies on substantially the same circle as the body 21 of the ring (which also applies to the arm 85), whereas in the small dimension condition, as shown in FIG. 8, the lever 83 and the arms 85 and 86 project from said ring.

To make the lever 83 easier to actuate and to make the equipment more maneuverable, the lever and the hinge zones 88 and 89 are molded to be greater in thickness than the remainder of the body 21, the lip 22, and the web constituting the arms 85 and 86, which arms are also curved to correspond to cut-outs 90 and 91 in the half-rings 80a and 80b for receiving said arms (FIGS. 9 and 10).

This embodiment operates in similar manner to the embodiment described with reference to FIGS. 1 to 4. Once the bag-carrier is fixed to the body of the user by means of its base plate 12, the lever 83 is moved to the condition shown in FIG. 8: in this condition, the bag 40 may be presented to the bag-carrier and the bag rim 41 may be applied without force and without difficulty onto the sealing ring 24. The lever 83 is then caused to pivot in the direction of f about its hinge 88 (FIG. 8), thereby displacing the hinge 87 in the direction of arrow p, thus moving apart the two ends of the half-rings 80a and 80b adjacent to the split 81. When the lever 83 has finished pivoting, the condition is as shown in FIG. 9 where the sealing ring 24 is in contact with the bag rim 41, thereby fixing the bag in leakproof manner on the bag-carrier.

To separate the bag from the bag-carrier, the lever 83 is pivoted in the direction opposite to that described above, thereby changing from the condition shown in FIG. 9 to the condition shown in FIG. 8, thus restoring the split ring 80 to its small-sized condition and the resilient sealing ring 24 to its initial condition, thereby enabling the bag rim 41 to be withdrawn by moving it away from the bag-carrier.

Figure 12:
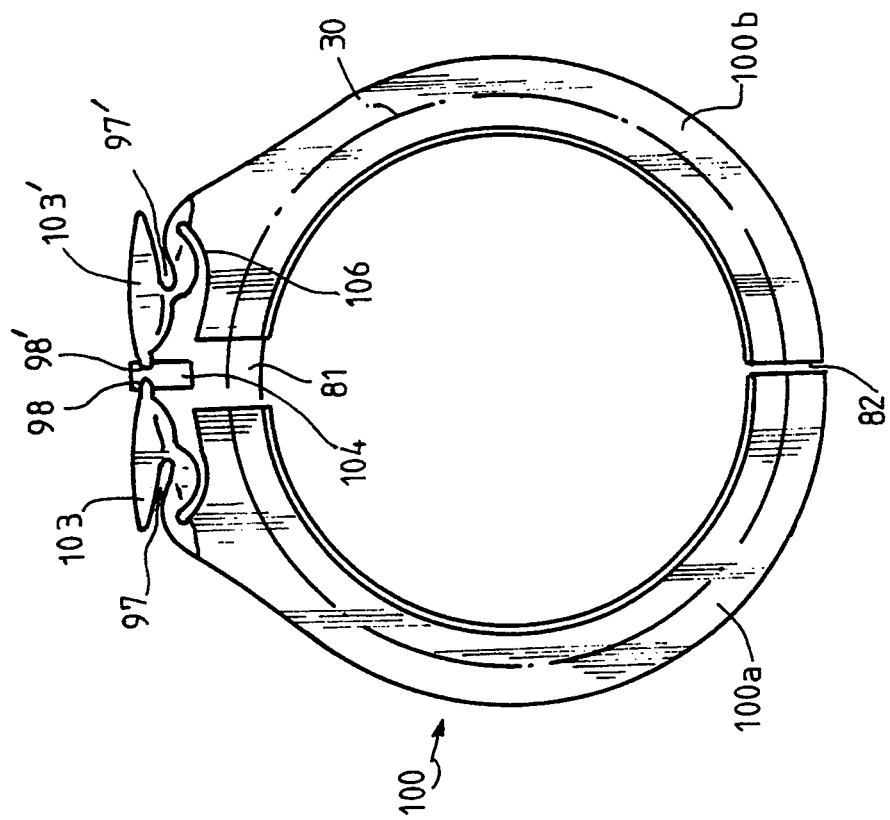
FIG. 12 is a view analogous to FIG. 11, but showing the part in another condition.
Figure 11:
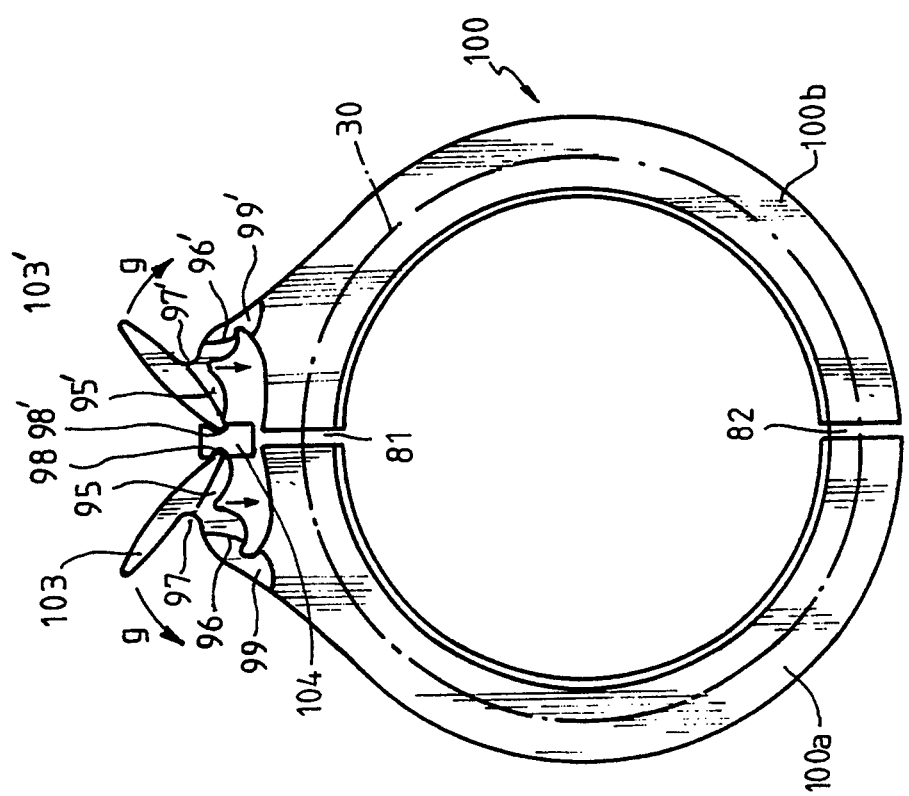
FIG. 11 is an elevation view of a component part of yet another embodiment of apparatus of the invention, the part being shown in a first condition.

FIGS. 11 and 12 show another embodiment similar to that of FIGS. 8 to 10, but in which the deformation means are doubled up, thereby making operation more flexible, but remaining identical in principle to the embodiment shown in FIGS. 8 to 10. In this embodiment, the actuator device is a ring 100 which is split at two diametrically opposite regions 81 and 82, thereby providing two half-rings 100a and 100b which are interconnected by two toggle mechanisms each constituted by a pair of arms referenced 95 and 96 for the first mechanism and 95' and 96' for the second mechanism, with each of the mechanisms being suitable for actuation by a respective lever 103 or 103'. As is clearly visible in FIGS. 11 and 12, the arms 95 and 96 are hinged to each other about a hinge 97 while the arms 95' and 96' are hinged to each other about a hinge 97'. The hinges to respective ones of the half-rings 100a and 100b are referenced 99 and 99', respectively. In addition, in this embodiment, the levers 103 and 103' are hinged to pivot about two axes referenced 98 and 98', which axes are fixed to a flange analogous to the flange 15 of the preceding embodiment by means of a part 104. In this embodiment, the size of the ring 100 is increased by actuating the two levers 103 and 103' in the directions of arrows g and g', thereby arriving at the configuration of FIG. 12, and thus retaining a bag on the bag carrier, whereas pivoting the levers in the opposite directions serves to release the bag from the bag-carrier.

In the embodiment shown diagrammatically in FIGS. 13 to 15, the arms 95a and 95'a (analogous to the arms 95 and 95' of the preceding embodiment) are shaped to provide respective horns 105 and 105a of narrower thickness than the arms from which they extend (FIG. 15), thereby enabling them to overlie a peripheral margin 44 of the flange 43 on the bag rim 41 (FIG. 14) when the bag is fixed to the bag-carrier. By having horns 105 and 105a suitable for co-operating with the margin 44 of the flange 43, retention of the bag on the bag carrier is enhanced, particularly as the bag fills up and its weight increases.

Figure 18:
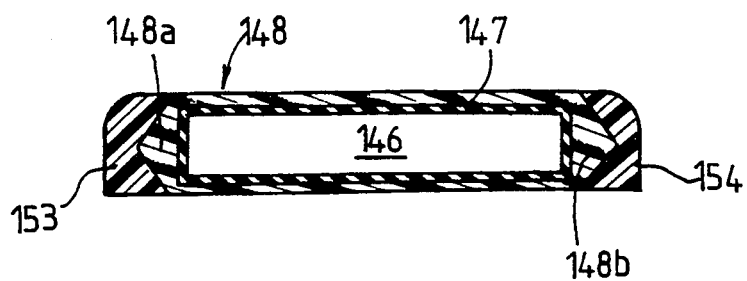
FIG. 18 is a section on line 18—18 of FIG. 16.
Figure 16:
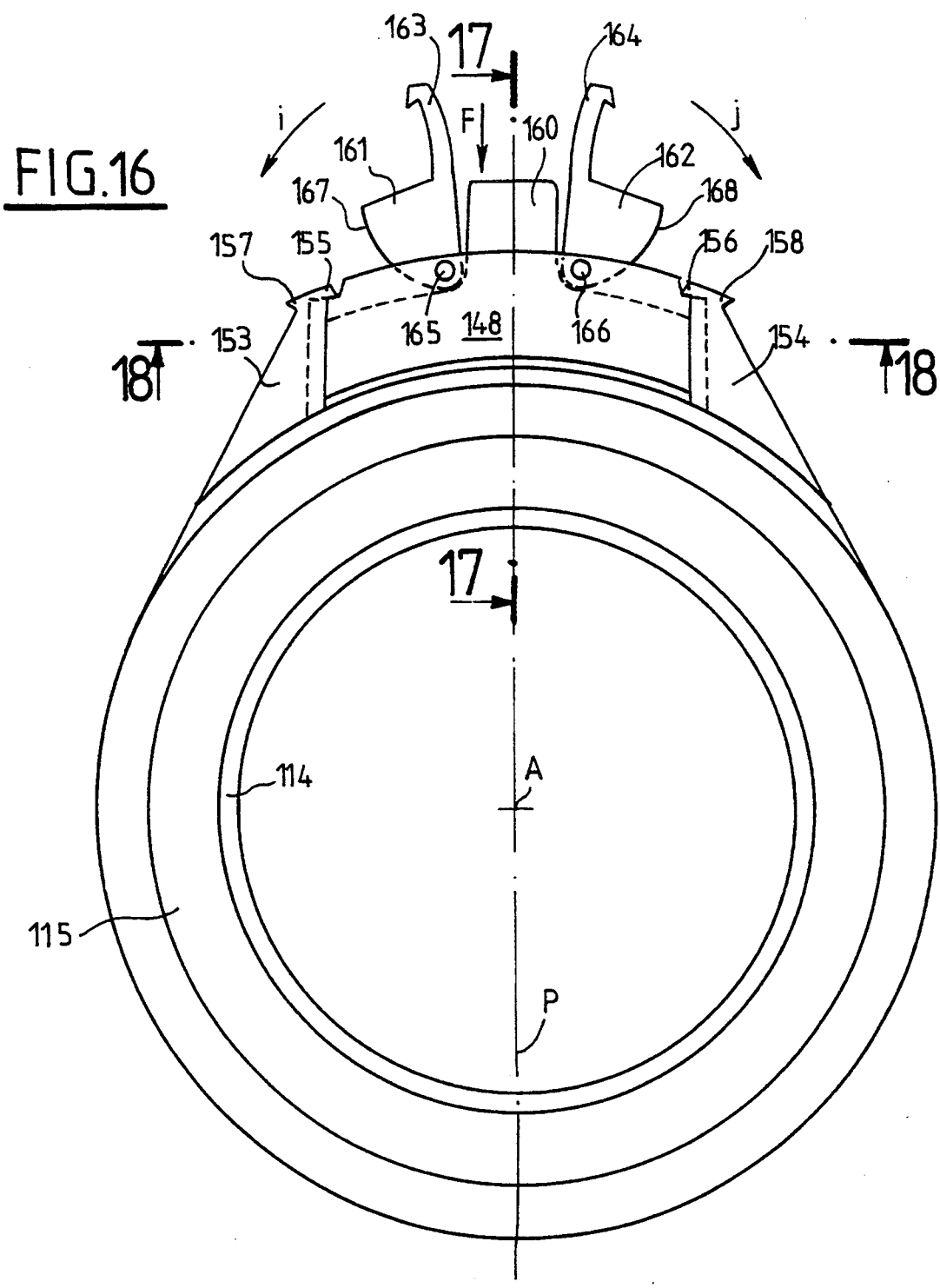
FIG. 16 is a diagrammatic elevation view of another embodiment of a bag-carrier for apparatus of the invention.
Figure 17:
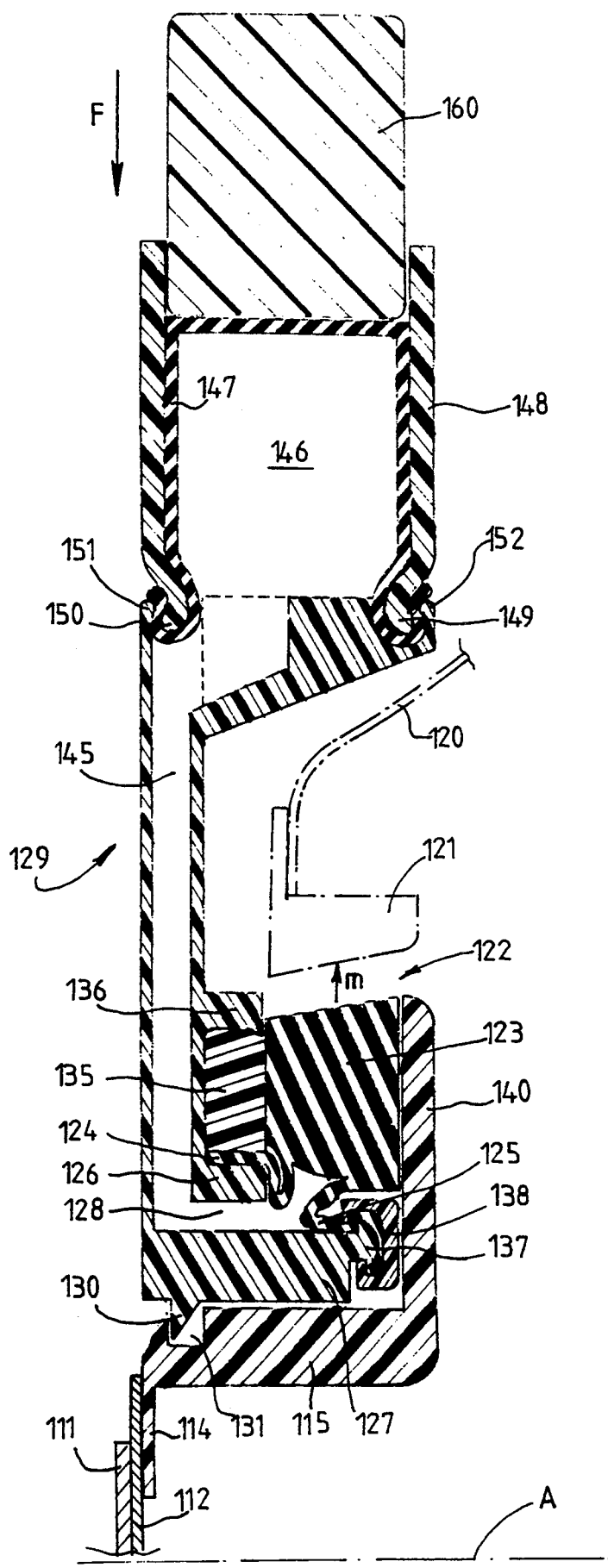
FIG. 17 is a section on line 17—17 of FIG. 16, but on a larger scale.

Reference is now made to FIGS. 16 to 18 relating to another embodiment. In these figures, the bag 120 is fixed to the bag-carrier 110 (having an adhesive base plate 112 protected by a film 111) by increasing the radial size of a sealing means 122 comprising a sealing ring per se 123 having a right cross-section that is somewhat trapezium-shaped with two resilient flexible membranes or lips 124 and 125 projecting therefrom and fixed to two separate walls 126 and 127 of the bag-carrier, thereby delimiting a chamber 128 which is adjacent to the sealing ring 123. The walls 126 and 127 are provided on a body 129 which is integral with a sleeve 115 of the bag carrier (analogous to the sleeve 17 of the embodiments of FIGS. 1 to 4) or which are mounted to rotate relative thereto by means of a rib 130 received in a groove 131 in said sleeve, with the membrane 124 being fixed to the wall 126 by a ring 135 which clamps on its inside against the wall 126 by bearing against a lip at right angles 136 which is parallel to said wall (FIG. 17), while the membrane 125 is secured to the "mushroom-section" wall 127 by a spring clip 138. The assembly is protected by a flange 140 which is integral with the sleeve 115 and which projects from the free end thereof that is distant from its flange 114, and extends substantially parallel thereto. To change the volume of the chamber 128 (thereby displacing the sealing ring 123 in the direction of arrow m thus increasing its radial size so that it bears against the bag rim 121 when the bag is applied to the bag-carrier), the invention provides for the chamber to communicate with a space of given volume 146 via channels 145. In the embodiment described and shown, the space 146 is formed by an enclosure 147 in a box 148 whose peripheral edges 149 and 150 are fixed to portions 151 and 152 of complementary shape on the body 129. The edges 149 and 150 are also clamped via a rolled edge which is crimped to the free edges of the enclosure 147. Two brackets 153 and 154 project from the body 129 symmetrically about a diametral plane p of the equipment and serve to hold the ends of the box 148 by means of ribs having substantially triangular right cross-sections 148a and 148b of said box interfitting (FIG. 18) in grooves of complementary shape on the brackets, with hooks 155 and 156 on said brackets preventing radial outwards displacement of the box, said brackets also having hooks 157 and 158 on their outside surfaces.

The box 148 slidably receives a piston 160 suitable for being displaced radially in response to actuation from one or two cam levers 161 and 162, which levers have operating surfaces 167 and 168, are provided with respective arms 163 and 164, and are pivotally mounted on the box 148 about axes 165 and 166.

To implement such equipment, the bag-carrier 110 is initially fixed to the body of the user by means of a base initially fixed to the body of the user by means of a base plate 112. To install a bag 120, the bag is presented to face the bag-carrier 110 and the bag rim 121 is placed around the sealing ring 123 without applying pressure to the region around the stoma, i.e. without causing the user any pain. The two levers 161 and 162 are then pivoted about their axes 165 and 166 as shown by arrows i and j in FIG. 16, thereby displacing the piston 160 towards the axis A of the bag-carrier, i.e. in the direction of arrow F in FIGS. 16 and 17. This piston movement deforms the enclosure 147 and the fluid (gas or liquid) contained inside the space 146 is conveyed by the channels 145 to the chamber 128 whose volume increases, thereby giving rise to radial displacement such that the sealing ring 123 moves away from the sleeve 115. When the sealing ring comes into contact with the bag rim 121 (made of relatively rigid material) it bears thereagainst, thereby obtaining the desired leakproof fixing of the bag 120 on the bag-carrier 110. The system is maintained in its operated condition by the fact that the arms 163 and 164 of the levers 161 and 162 are provided with hooks at their ends that are complementary to the hooks 157 and 158 on the brackets 153 and 154. To remove the bag 120 from the bag-carrier 110, the opposite procedure is performed, in which the levers 161 and 162 are unlocked and then moved in the direction opposite to that described above.

In the variant shown in FIGS. 17A and 17B, the inside diameter φ1 of the bag rim 121 is smaller than the outside diameter φ2 of the flange 140 but larger than the outside diameter φ3 of the sealing ring 123, with the length of the bag rim 121 (as measured parallel to its axis of symmetry) being less than the thickness of the ring 123. To install the bag, advantage is taken of the deformability of the bag rim 121 which is made of thermoplastic material. The rim is inserted in the gap between the inside face of the flange 140 and the lip 136 (FIG. 17B) in much the same way as a tire is installed on the rim of a wheel, but naturally without the same difficulty. This ensures that the bag rim 121 is properly positioned around the sealing ring 123 without any danger of the bag rim moving axially while leaving it very free in rotation about said sealing ring, thus making it possible to fix the bag in leakproof manner without any risk of error in placing the bag relative to the bag-carrier.

The structure of the equipment shown in FIGS. 19 and 20 is very similar to that described above, and corresponding parts are given the same references. However, in this embodiment, the piston 160a is subjected to the action of a single pivoting lever 170 whose hook 171 at its end opposite to its pivot is suitable for co-operating with the hook of complementary shape 158 on the bracket 154.

In the embodiment shown in FIGS. 21 and 22 (where parts that correspond to those of FIGS. 16 to 18 are given the same references as on those figures), the piston 160b is not mounted to move radially, but to move in a direction parallel to the axis of the sleeve 115 when a lever 172 is actuated to cause said piston 160b to penetrate to a greater or lesser extent inside the box 148'.

In the embodiment shown in FIGS. 23 to 26, parts which are identical to those of the embodiment of FIGS. 16 to 18 are given the same references as therein, and the channels 145 connect to the chamber 128 to an enclosure or space 175 which is closed by a plug 176. The enclosure 175 is fitted to a flexible deformable tube 177 having a valve 178 placed thereon which is in turn connected to an endpiece 179 of the conical type or of the Luer type for connection to a source of fluid under pressure. The valve 178 is provided with a vent 180 for releasing air when the endpiece 179 is in a first position, while the valve 178 allows fluid to be inserted into the enclosure 175 for controlling radial displacement of the sealing ring 123 against the bag rim 121 when said endpiece is in a second position. As in the preceding embodiments, the bag rim is rigid enough to accept the sealing pressure applied to it in this way. To make the equipment easier to use, the invention provides for the concertina-like flexible tube 177 to be held in place close to the bag-carrier on which it is installed by means of a clip 181 (when the bag is installed on the bag-carrier) while allowing the tube 177 to be moved away for the purpose of connecting the endpiece 179 to the source of fluid under pressure.

In the embodiment shown very diagrammatically in FIG. 27, which is mostly identical to that described immediately above with reference to FIGS. 23 to 26, a non-return valve 185 for retaining pressure and a bellows tube 186 are installed between the valve 178' and the enclosure 175 into which the channels 145 open out. The valve 185 and the bellows tube 186 constitute a pump system for inflating the chamber 128 via the enclosure 175 and the channel 145. In this embodiment, the radial size of the sealing ring 123 is increased by applying a pushbutton 187 on the valve 178' (e.g. by screwing it thereon) and then by deforming the bellows tube 186 longitudinally like a pump, with inflation pressure, and consequently the pressure providing leakproof application of the bag-carrier 110 against the bag 120, being maintained after the pushbottom 187 has been withdrawn from the valve 178', and with the bag being disassembled from the bag-carrier by putting the enclosure 175 into communciation with the atmosphere, most simply by withdrawing the plug 176 by unscrewing it.

Figure 28:
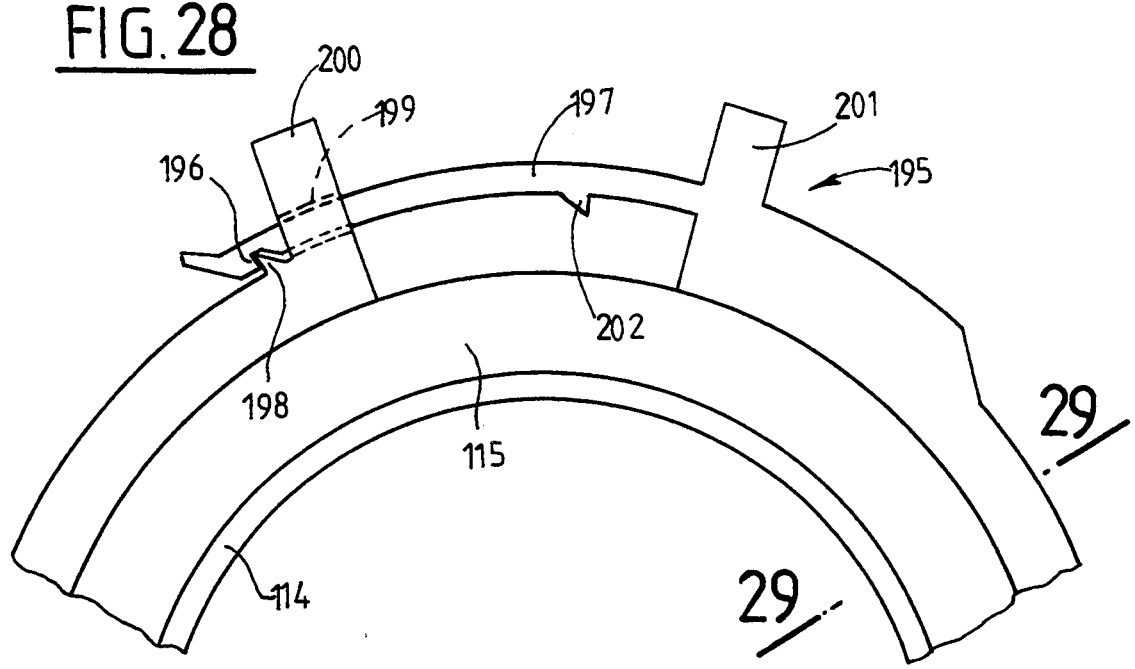
FIG. 28 is a view analogous to that of FIGS. 19 and 21, but for yet another embodiment.
Figure 29:
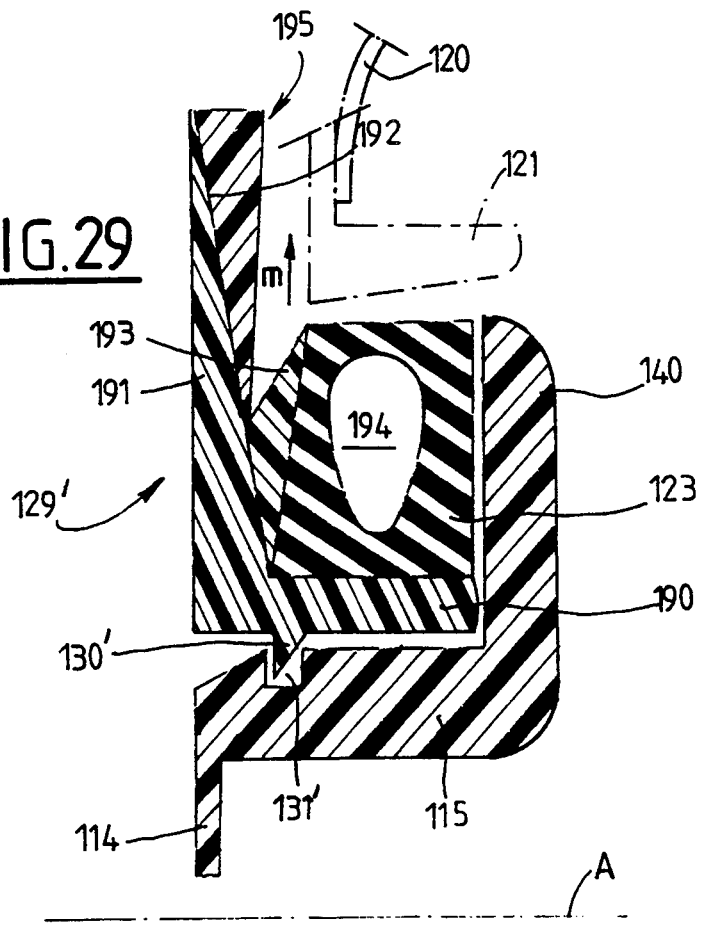
FIG. 29 is a diagrammatic fragmentary section on line 29—29 of FIG. 28, and on a larger scale.

In the embodiment shown in FIGS. 28 and 29 the radial size of the sealing ring 128 is obtained by wedge type mechanical means. More precisely, in this embodiment, the invention provides a body 129' performing the same role as the body 129 of the embodiment of FIGS. 16 to 18 in the form of a cylindrical wall 190 suitable for fixing to the sleeve 115 either without any possibility of relative motion or else, in a variant, mounted with the possibility of rotating relative to said sleeve by means of a rib 130' received in a groove 131' in the sleeve 115. The wall 190 is integral with a base 191 extending substantially perpendicularly to the axis A of the equipment and which has an outside face 192 that slopes relative to said axis. A washer 193 of triangular right cross-section is placed on the base 191 concentrically with the wall 190 and adjacent thereto. The washer co-operates with the flange 140 of the sleeve 115 to form a groove in which the sealing ring 123 is received. The right cross-section of the sealing ring is somewhat trapezium-shaped, and the sealing ring is advantageously made of an elastomer-based resilient material (whose hardness preferably lies in the range 20 to 40 on the Shore A scale) or else of a plastomer material in which case it is particularly appropriate to use a foam or cellular material having an integral skin.

Whatever the material chosen, the sealing ring 123 is either a "solid" body, or else in a variant it is a "toroidal" body enclosing a cavity 194 filled with an incompressible fluid such as water.

In this embodiment, in order to increase the radial size of the sealing ring 123, the invention provides an operating member 195 which is associated with the bag-carrier 110 and which is constituted by a split ring of triangular right cross-section which is applied to the base 191 where it is maintained in its open condition (shown in FIG. 28) by co-operation between a hook 196 provided at the end of a tongue 197 projecting from one of the ends of the ring and a catch 198 provided on the opposite end of said ring, with the tongue 197 being suitable for sliding through an opening 199 in the end lug 200 on which the catch 198 is mounted. The end of the ring 195 opposite to the end carrying the lug 200 is shaped to have a lug 201, and in the vicinity of this lug the tongue 197 carries a tooth 202.

To operate the equipment, once the bag-carrier has been fixed to the body of the patient, a bag 120 is applied to the bag-carrier with the bag rim 121 facing the sealing ring 123, or else in a variant it is installed in the manner described above with reference to FIGS. 17A and 17B. This is done while the ring 195 is in its open condition as shown in FIG. 28 (i.e. the hook 196 is engaged with the catch 198), the ring therefore does not co-operate with the washer 193 until the lugs 200 and 201 are moved towards each other so that the tongue 197 slides in the passage 199 and the ring 195 engages beneath the washer 193. The sealing ring 123 as held in place by the flange 140 and by the cylindrical wall 190 then deforms in the direction of arrow m, i.e. its radial size increases until it comes into contact with the bag rim 121 which is made of a relatively rigid material so as to constitute a thrust surface providing sealing and locking for the bag on the bag carrier.

The assembled condition is retained so long as the tooth 202 on the tongue 197 co-operates with the catch 198 to retain the member 195 in its closed position, and releasing the tooth 202 relative to said catch enables the resilient member 195 to return to the condition shown in FIG. 28 in which the bag 120 can be removed from the bag-carrier 110 since the sealing ring 123 also returns to its initial condition.

Figure 30:
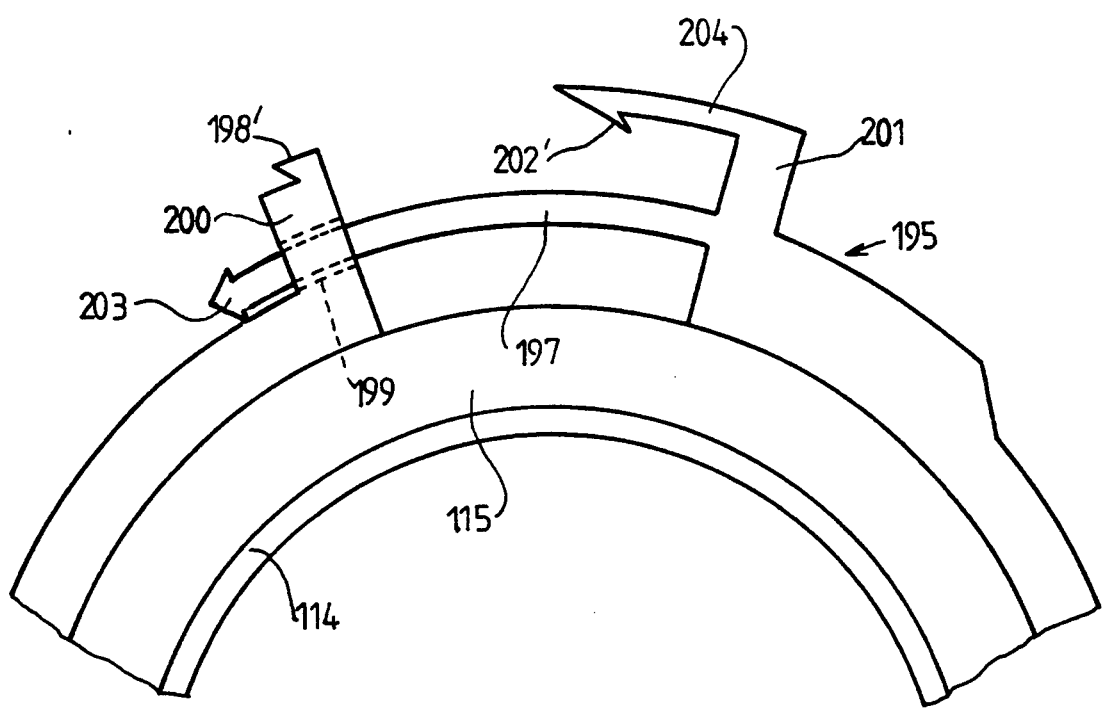
FIG. 30 is a view analogous to FIG. 28, but showing a variant.

In the embodiment shown diagrammatically in FIG. 30, a tooth 202' (analogous to the tooth 202 of the embodiment shown in FIGS. 28 and 29) is associated with the lug 201 and is suitable for co-operating with a catch 198' (analogous to the catch 198) provided on the lug 200. In this embodiment which operates in the same way as that described above with reference to FIGS. 28 and 29, the tongue 197 having a harpoon-like tip 203 slides through the passage 199 as the lugs 200 and 201 move towards each other under pressure from the user's fingers until the tooth 202' engages the catch 198', with the tooth 202' being disengaged from the catch 198' merely by lifting the end of the tongue 204 carrying said tooth, thereby enabling the resilient member 195 to return to its condition shown in FIG. 30.

By allowing the control member 195 to rotate freely about the axis A of the equipment, when in the open condition as shown in FIGS. 28 and 30, the user is given the advantage of positioning the lugs 200 and 201 in the best possible position for user comfort and/or for operating the lugs.

We claim:

1. Stoma equipment comprising a bag-carrier for fixing around an artificial opening in the body of a user by means of a base plate provided with an adhesive or with a pressure-sensitive adhesive rubber or with any equivalent means, together with a bag for collecting body wastes and/or fluids and suitable for being removably assembled to a sleeve or collar of the bag carrier by means of a rim on the bag, wherein the bag is fixed on the bag-carrier by deforming sealing means whose radial size is increased by operating an appropriate actuator device connected to said rim of the bag.

2. Equipment according to claim 1, wherein the actuator device is a split ring which is associated with the sealing means constituted by a sealing ring of resilient material interposed between the bag rim and the split ring when the bag is applied to the bag-carrier.

3. Equipment according to claim 2, wherein the split ring is integrally formed with said actuator means constituted by a lever hinged on the split ring and controlling a toggle type mechanism.

4. Equipment according to claim 1, wherein the actuator device is constituted by two half-rings which are associated with the sealing means made of resilient material interposed between the bag rim and the half-rings when the bag is placed on the bag-carrier.

5. Equipment according to claim 4, wherein each half-ring is integral with said actuator means constituted by a lever hinged thereto and controlling a toggle mechanism.

6. Equipment according to claim 4, wherein the two half-rings are connected to each other by a toggle mechanism having two arms hinged to each other about a hinge and which are hinged to respective ones of the half-rings by other hinges, the first hinges of which also constitutes the fulcrum of a lever.

7. Equipment according to claim 4, wherein the two half-rings are interconnected by two toggle mechanisms, each constituted by a pair of arms hinged together about a hinge and hinged to the half-rings via respective hinges, fulcrums for levers being formed about two hinge axes.

8. Apparatus according to claim 2, wherein the sealing ring has a trapezium-shaped right cross-section and is engaged around a lip on the split ring, deformation of the split ring during operation of the actuator means deforming the sealing ring until it is applied in leakproof manner against the bag rim.

9. Equipment according to claim 1, wherein the bag rim is made of a plastic material that is rigid enough to accept a clamping force developed by the sealing means with which its inside face of generally hyperbolic section co-operates when the bag is assembled to the bag-carrier.

10. Equipment according to claim 1, wherein to mount the actuator device on the bag-carrier, the bag-carrier has a groove delimited by a collar which surrounds the stoma when the equipment is in use, and by two flanges which are substantially parallel to each other and perpendicular to the axis of the collar, a first one of the flanges co-operating in retaining the sealing ring and a second one of the flanges serving firstly to fix the bag-carrier to the base plate and secondly to guide and/or retain the actuator device on said bag carrier.

11. Equipment according to claim 10, wherein the flange for guiding and/or retaining the actuator device is provided with slots which receive studs on the actuator device.

12. Equipment according to claim 1, wherein the sealing means is a split ring shaped to have projections at its periphery suitable for co-operating with hollows or a groove of complementary shape provided in the bag rim.

13. Equipment according to claim 1, wherein the same elastically deformable member acts both as the sealing ring and as the actuator device.

14. Equipment according to claim 13, wherein the elastically deformable member is an inflatable and deflatable toroidal chamber, and wherein the inflation means for inflating the toroidal chamber is a syringe type device, a supply of gaseous fluid under pressure such as a portable compressed air cylinder, or a hydraulic device in which the displacement of a lever serves to transfer a given volume of liquid into or out from said chamber.

15. Apparatus according to claim 1, wherein the sealing means whose radial size is increased comprises a sealing ring mounted to move radially relative to the sleeve of the bag-carrier and away from said sleeve when the volume of a chamber adjacent to said sealing ring is increased.

16. Equipment according to claim 15, wherein the volume of the chamber adjacent to the sealing ring is increased by inserting a quantity of fluid into said chamber in addition to the fluid that it contained initially, said insertion being obtained by locally deforming a space of given volume.

17. Equipment according to claim 15, wherein the sealing means is a solid or hollow component having lips or membranes for fixing to a body integral with the bag-carrier and including means enabling the volume of the chamber adjacent to said sealing ring to be modified.

18. Equipment according to claim 17, wherein the body has channels opening out into an enclosure whose volume can be modified and into which a fluid under pressure can be inserted.

19. Equipment according to claim 16, wherein the space is delimited by a wall of resilient material against which a piston is disposed to act, displacement of the piston being controlled by said actuating comprising one or more levers.

20. Equipment according to claim 19, wherein the space is enclosed in a box fixed to the bag-carrier by brackets, and wherein said brackets have hooks suitable for co-operating with complementary hooks on the piston actuating lever(s) to hold said lever(s) in a position corresponding to the bag being assembled to the bag-carrier.

21. Equipment according to claim 15, wherein the space for feeding the variable volume chamber adjacent to the sealing ring via the channels may be connected to a source of fluid under pressure by a valve device via a flexible deformable tube.

22. Equipment according to claim 21, wherein the valve device is connected to a non-return valve itself connected to a bellows type tube for inflating the space by means analogous to a pump.

23. Equipment according to claim 15, wherein the said actuator device comprises a split ring and a washer adjacent to said sealing means, the split ring and the washer interacting by a wedge effect to deform said sealing means radially.

24. Equipment according to claim 23, wherein the split ring has actuator lugs at its ends for moving said ends towards each other and latches, hooks, or catches for holding it in an open position or in a closed position.

25. Equipment according to claim 24, wherein the split ring also includes a tongue fixed to one of the lugs and slidably received in a passage through the other lug to guide said lugs relative to each other while they move towards each other and/or while they move away from each other.

26. Equipment according to claim 1, wherein the sealing means and the body carrying the sealing means are mounted to rotate relative to the sleeve of the bag carrier.

27. Equipment according to claim 1, wherein the sealing means is made of an elastomer type material and/or of a cellular or foam type plastomer having an integral skin.

28. Equipment according to claim 27, wherein the sealing member is a solid or a hollow body made of an elastomer material having hardness lying in the range 20 to 40 on the Shore A scale.

29. Equipment according to claim 15, wherein the sealing means is held on the bag-carrier against axial displacement by means of flange, and wherein the inside diameter of the bag rim is smaller than the outside diameter of said flange but larger than the outside diameter of the sealing means.

30. Equipment according to claim 1, wherein said bag carrier comprising a base plate provided with an adhesive or with a pressure-sensitive adhesive rubber or with equivalent means for fixing to the body of a user, said bag-carrier having a sleeve for insertion inside the bag rim in the assembled condition of the equipment, said bag-carrier including and said sealing means being disposed around the sleeve.

31. Equipment according to claim 1, comprising a rim around an opening of one of its walls made of a relatively rigid material and which is directed towards the inside of the bag.

32. Equipment according to claim 31, wherein the rim has a cross-section the internal surface of which is curved and of a substantially generally hyperbolic contour.

* * * * *